United States Patent
Al-Jazaeri et al.

(10) Patent No.: US 10,426,634 B1
(45) Date of Patent: Oct. 1, 2019

(54) EXPANDABLE INTERVERTEBRAL CAGE

(71) Applicant: KING SAUD UNIVERSITY, Riyadh (SA)

(72) Inventors: Ayman Hassan Al-Jazaeri, Riyadh (SA); Amro Fayez Al-Habib, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/268,393

(22) Filed: Feb. 5, 2019

(51) Int. Cl.
*A61F 2/44* (2006.01)
*A61F 2/30* (2006.01)

(52) U.S. Cl.
CPC .... *A61F 2/447* (2013.01); *A61F 2002/30261* (2013.01); *A61F 2002/30579* (2013.01); *A61F 2002/30622* (2013.01); *A61F 2002/30848* (2013.01); *A61F 2002/30904* (2013.01); *A61F 2002/4475* (2013.01)

(58) Field of Classification Search
CPC ..................... A61F 2/447; A61F 2/4455; A61F 2002/30261; A61F 2002/30579; A61F 2002/30622
See application file for complete search history.

(56) References Cited

U.S. PATENT DOCUMENTS

| | | | |
|---|---|---|---|
| 5,665,122 A | 9/1997 | Kambin | |
| 9,603,717 B2 | 3/2017 | Ibarra et al. | |
| 9,801,640 B2 * | 10/2017 | O'Neil | A61B 17/1671 |
| 10,137,007 B2 * | 11/2018 | Dewey | A61F 2/4425 |
| 2013/0158664 A1 * | 6/2013 | Palmatier | A61F 2/447 623/17.16 |
| 2013/0158669 A1 | 6/2013 | Sungarian et al. | |
| 2014/0336764 A1 | 11/2014 | Masson et al. | |
| 2015/0272743 A1 * | 10/2015 | Jimenez | A61F 2/447 623/17.16 |
| 2016/0262907 A1 | 9/2016 | Jimenez et al. | |
| 2016/0324651 A1 | 11/2016 | Masson et al. | |
| 2018/0325697 A1 | 11/2018 | Moskowitz et al. | |

OTHER PUBLICATIONS

"Elite(tm) Expandable", (c) 2017 Spineology Inc. https://www.spineology.com/united-states/our-products/elite.
"Caliber(R)", (C) 2018 Globus Medical inc. http://www.globusmedical.com/portfolio/caliber/.

* cited by examiner

*Primary Examiner* — Ellen C Hammond
(74) *Attorney, Agent, or Firm* — Richard C. Litman

(57) ABSTRACT

The expandable intervertebral cage includes an upper block and a lower block movable relative to each other. The lower block defines a cam surface and the upper block defines a cam follower surface. Linkages connecting the upper and lower blocks maintain contact between the cam and cam follower surfaces. By rotating a screw, which extends through the lower block, the cam follower surface of the upper block is pushed along the cam surface of the lower block, thus resulting in vertical and horizontal displacement between the upper and lower blocks. Proximal and distal yokes in the blocks define protrusions in the cam and cam follower surfaces. When the cam follower surface slides along the cam surface, the protrusions cause vertical and angular displacement in the upper block, providing distraction, reduction, and lordosis of attached vertebra.

13 Claims, 5 Drawing Sheets

EXPANDABLE INTERVERTEBRAL CAGE

BACKGROUND

1. Field

The disclosure of the present patent application relates to spinal repair, and particularly to an expandable intervertebral cage for performing distraction, reduction, and segmental lordosis of the lumbar spine.

2. Description of the Related Art

Degenerative disc disease is one of the most common causes of low back and neck pain. Degenerative disc disease starts with reduced water content within the disc. Subsequently, the disc becomes less elastic and loses its ability to withstand mechanical stress. The resulting reduction in disc height starts an inflammatory process affecting the vertebral segment; a condition known as degenerative disc disease. These involved structures represent significant sources for low back pain. If the loss of disc height is associated with reduction in the height of the nerve foramena, the exiting nerve root can be compressed, giving rise to radicular pain (sciatica) or nerve weakness. These changes are part of the aging process, with some people being affected earlier than others.

Spondylolisthesis, or sliding of the upper vertebra anteriorly relative to the lower one, can be a result of degenerative spine disease. When the condition is associated with advanced facet degeneration, spondylolisthesis can develop. The situation will then lead to low back pain that worsens with standing. Adjacent nerve roots could be also stretched or compressed, leading to radicular pain, parasthesia, or weakness. Spondylolisthesis could lead to functional disability and poor quality of life.

Although lumbar decompression and instrumented fusion is an effective and proven treatment for symptomatic spondylolisthesis, the current literature provides insufficient evidence to recommend an optimal fusion approach. A commonly used surgical approach in interbody fusion technique is an open transforaminal lumbar interbody fusion (TLIF) with posterolateral fusion. It provides a restoration to the height of the intervertebral segment and indirect decompression of the nerve roots. The intervertebral cage also provides a structural support that is particularly valuable in osteoporotic patients. The intervertebral cage may be used for support in an intervertebral bone graft, and enhances fusion.

In recent years, intervertebral cages have gained popularity due to their ease of insertion and ability to distract the vertebral space to the desired height. Some expandable intervertebral cages were introduced to improve spinal alignment by inducing lordosis. However, they were not designed to correct the associated spondylolisthesis, which was the original problem affecting the vertebral segment. The reduction in spondylolisthesis is often tried with intervertebral distraction and by manipulating the pedicle screws involved in segmental fixation. This segment often goes back to the original listhesis (sliding) position because the cages were not designed to reduce the vertebral segment. Moreover, the resulting manipulation of pedicle screws could put significant stress on the screws, weakening their bone purchase.

Thus, an expandable intervertebral cage solving the aforementioned problems is desired

SUMMARY

The expandable intervertebral cage includes an upper block and a lower block that are movable relative to each other. The lower block defines a cam surface and the upper block defines a cam follower surface. Linkages connecting the upper and lower blocks maintain contact between the cam and cam follower surfaces. By rotating a screw, which extends through the lower block, the cam follower surface of the upper block is pushed along the cam surface of the lower block, thus resulting in vertical and horizontal displacement between the upper and lower blocks. Proximal and distal yokes in the blocks define protrusions in the cam and cam follower surfaces. When the cam follower surface slides along the cam surface, the protrusions cause vertical and angular displacement in the upper block relative to the lower block. Accordingly, the horizontal, vertical, and angular displacement of the upper block relative to the lower block provides distraction, reduction, and lordosis of attached vertebra.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
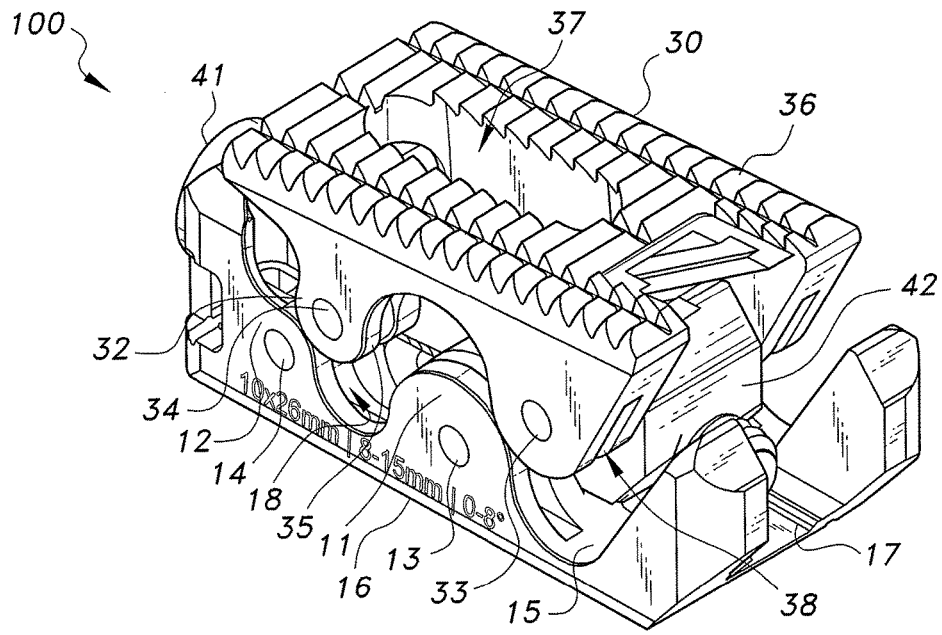
FIG. 1A is a perspective view of an expandable intervertebral cage.
Figure 1B:
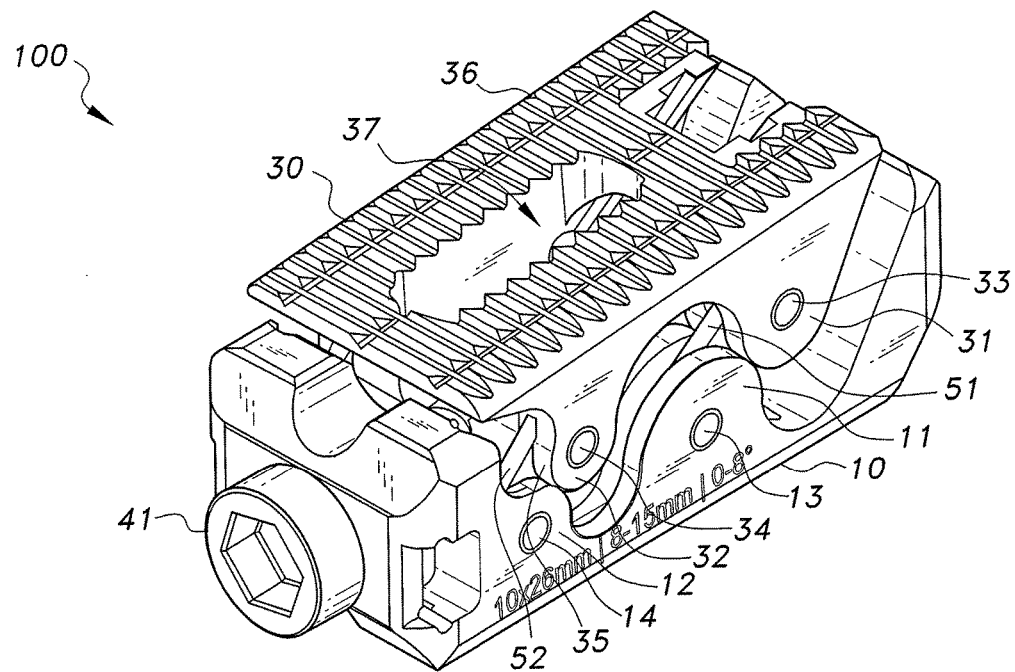
FIG. 1B is a perspective view the expandable intervertebral cage of FIG. 1 as seen from the opposite side.

As seen in FIGS. 1A and 1B, the expandable intervertebral cage 100 includes an upper block 30 and a lower block 10 connected by linkages 51, 52. Contoured surfaces 15 on opposing sides of the lower block 10 act as a cam and interact with contoured surfaces 35 on the upper block 30 that act as a cam follower. By rotating a screw 41 attached to the lower block 10, a nut 42 attached to both blocks 10, 30 pushes the upper block 30 across the camming surfaces 15 of the lower block 10. When the cam follower surfaces 35 of the upper block 30 are moved across the cam surfaces 15 of the lower block 10, the upper block 30 changes horizontal position, vertical position, and angular orientation relative to the lower block 10. Different contours on the cam surfaces 15 and cam follower surfaces 35 will result in changing the positional and angular displacement of the upper block 30 in relation to the lower block 10 during and after expansion, thus allowing the cage 100 to be modified for patient specific scenarios.

The lower block 10 includes a lower bone contacting surface 16 having hooks, spikes or a porous/roughened surface to provide for attachment to the bone. The center of the bone contacting surface 16 includes an opening for accepting bone grafting material and/or ingrowth from the contacted bone. A front or proximal end of the lower block 10 extends upward to provide a hole 61 (shown in FIG. 4A) that acts an anchoring point for the head of the screw 41. Two anchoring pins 43 immediately above and below the screw 41 (best seen in FIG. 2) extend through apertures in the lower block 10 and are seated within an annular groove defined in the outer surface of the screw 41. The pins 43 allow the screw 41 to rotate around its axis, while preventing the screw 41 from translating along its axis. Therefore, when the screw 41 is rotated, the screw 41 will remain in the same position relative to the lower block 10, while the nut 42 is moved axially by the screw threads. The nut 42 has a dovetail shape on its lower end that slides within a dovetail groove 17 that extends along the length of the lower block 10. Rotating the screw 41 moves the nut 42 along the dovetail groove 17.

Opposing sides of the lower block 10 define cam surfaces 15 that extend from the front or proximal to rear or distal ends of the block 10, and a passageway extends between the cam surfaces 15. Both cam surfaces 15 have identical shapes and are each defined by a proximal yoke 12 and a distal yoke 11. At least a portion of the cam surface 15 defined by each yoke 11, 12 is circular and has a hinge pin 13, 14 located at the center of the circle. A channel 18 extends along the length of each yoke 11, 12 to accommodate the linkage 52 and the linkage 51 that are each connected to a respective pin 14, 13. A linkage 51, 52 is connected to each yoke 11, 12 at the hinge pin 13, 14, which is at a center of each circular portion. The linkages 51, 52 hold the cam and cam follower surfaces 15, 35 against each other when the arcuate portions of the surfaces 15, 35 are contacting.

Figure 3A:
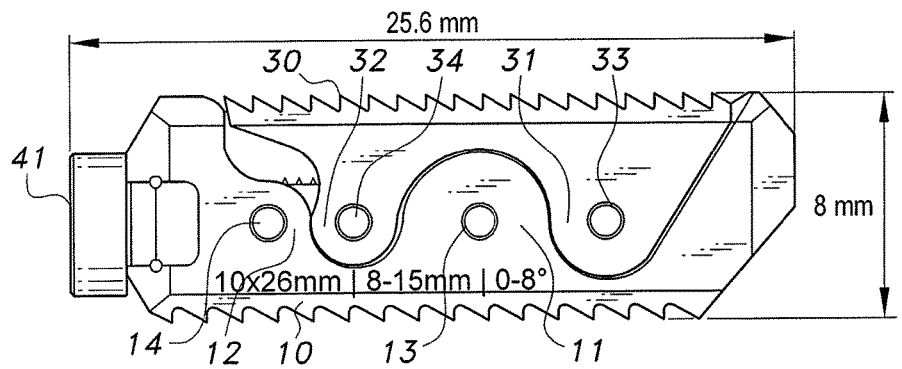
FIG. 3A is side view of the expandable intervertebral cage of FIG. 1, shown in a fully compressed configuration.
Figure 3B:
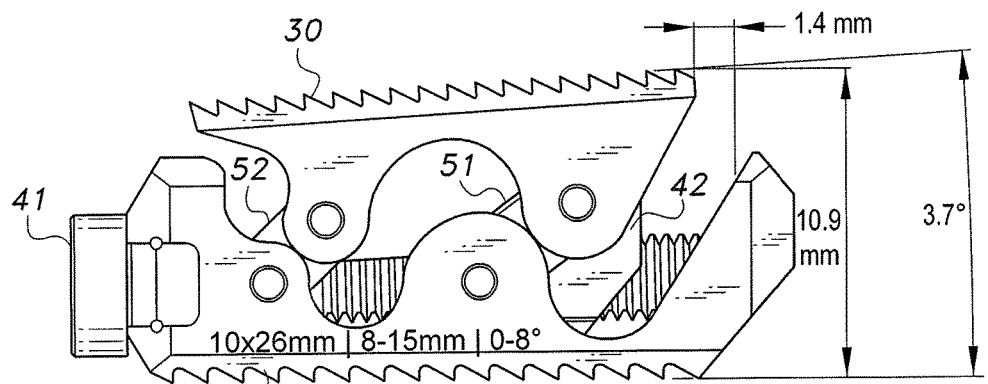
FIG. 3B is side view of the expandable intervertebral cage of FIG. 1, shown in a half-expanded configuration.

The upper block 30 includes an upper bone contacting surface 36 having hooks, spikes or a porous/roughened surface to provide for attachment to the bone. The center of the bone contacting surface 36 includes an opening 37 that is designed to accept bone grafting material and/or ingrowth from the contacted bone. As seen in FIGS. 3A-3B, the spikes on the upper block 30 are pointed forward and the spikes on the lower block 10 are pointed rearward. The range of motion of the cage 100 results in the upper block 30 moving relative to the lower block 10. By pointing the spikes in the direction of force for each block 10, 30, the spikes will dig into the contacted bone and move it along with the block 10, 30.

Opposing sides of the upper block 30 define cam follower surfaces 35 that extend from the front or proximal to rear or distal ends of the block 30, and a passageway extends between the cam follower surfaces 35. Both cam follower surfaces 35 have identical shapes, and each includes a proximal yoke 32 and a distal yoke 31. At least a portion of the surface of each yoke 31, 32 is circular and has a hinge pin 33, 34 located at the center of the circle. A channel 38 extends along the length of each yoke 31, 32 to accommodate the linkage 52 and the linkage 51 that are each connected to a respective pin 34, 33. Each linkage 51, 52 is connected at one end to each yoke 31, 32 at the hinge pin 33, 34, which is at a center of each circular portion defined by the yokes 31, 32, and to each respective opposite yoke 11, 12 at the hinge pin 13, 14. Accordingly, each linkage 51, 52 will hold the cam surface 15 and the cam follower surface 35 against each other when the arcuate portions of the yokes are contacting.

Figure 2:
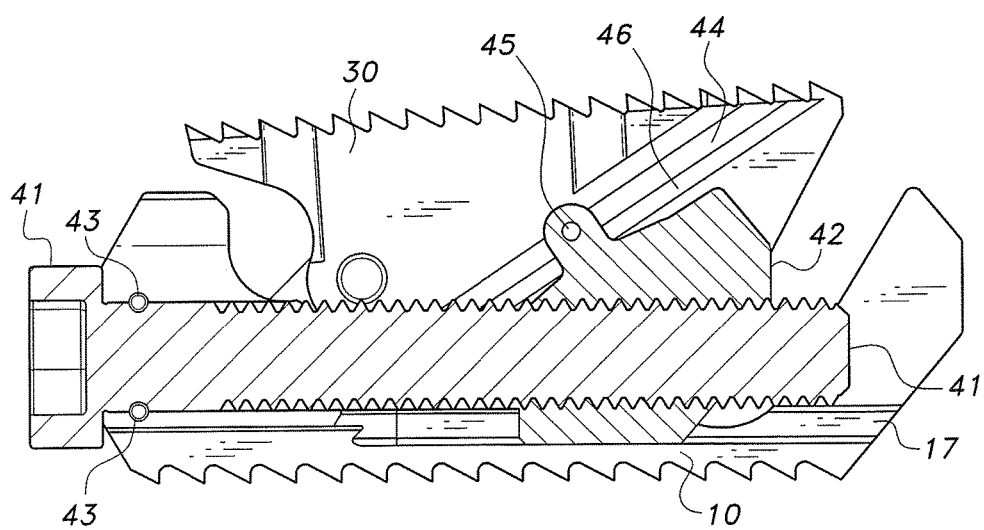
FIG. 2 is a side view in section of the expandable intervertebral cage of FIG. 1.

The inside walls of the passageway defined by the yokes 31, 32 of the upper block 30 include an angled flange 46 having a groove 44 extending parallel to the edge of the flange 46, as best seen in FIG. 2. Each wall on opposing sides of the passageway includes a flange and groove 44 that is a mirror replica of the opposing flange 46.

The lower surface of the flanges 46 bear against opposing sides of an upper surface of the nut 42 that sits within the passageway defined between the yokes 31, 32. When the screw 41 is rotated to pull the nut 42 towards the proximal end of the cage 100, the nut 42 is forced against the flange 46. Since the flange 46 is oriented at an upward angle, the nut 42 forces the upper block 30 upwards and proximally when the nut 42 moves proximally. The movement of the upper block 30 in relation to the lower block 10 is controlled by the interaction between the cam surfaces 15 and cam follower surfaces 35, as well as the linkage 52 and the linkage 51. The nut 42 includes an upper lug, which supports laterally projecting pins 45 that slide within the grooves 44 in the flanges 46 on both sides of the nut. When the screw 41 is turned in the direction that drives the nut 42 distally, the pins 45 pull the upper block 30 downward and distally through their interaction with the grooves 44.

Figure 3C:
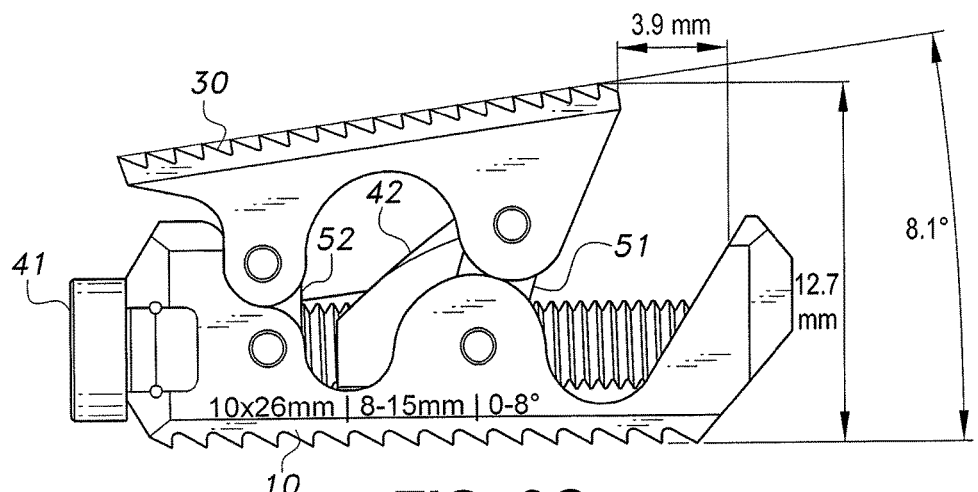
FIG. 3C is side view of the expandable intervertebral cage of FIG. 1, shown in a fully expanded configuration.

FIG. 3A-3C show the interaction between the upper block 30 and the lower block 10 as the cam follower surfaces 35 of the upper block 30 are slid across the cam surfaces 15 of the lower block 10. FIG. 3A shows the cage 100 at a minimal height, which would be set for insertion or extraction. The distal yoke 11 of the lower block 10 fits within a valley between the yokes 31, 32 of the upper block 30, and the yokes 31, 32 of the upper block 30 fit within valleys adjacent the yokes 11, 12 of the lower block 10. Rotating the screw 41 in a first direction pulls the nut 42 proximally, causing it to push against the flange 46 of the upper block 30 and force the upper block 30 proximally along the cam surfaces 15. The relative movement of the blocks 10, 30 is guided by the interacting cam and cam follower surfaces 15, 35 which are held together by linkages 52 that connect the proximal yokes 12, 32, and by linkages 51, which connects the distal yokes 11, 31. As seen in FIG. 3B, the initial movement of the nut 42 primarily moves the upper block 30 upward, since the interacting portions of the cam and cam follower surfaces 15, 35 are oriented in a primarily vertical direction. As shown in FIGS. 3A-3C, the distal yokes 11, 31 have larger radiuses than the proximal yokes 12, 32, which results in a larger distance between their hinge pins 13, 33. Therefore, the distal end of the upper block 30 will be pushed higher than the proximal end to accommodate this larger distance. As seen in FIG. 3C, when the device is fully extended, the proximal end of the upper block 30 is higher than the distal end of the upper block 30 relative to the lower block 10, which results in the upper surface of the upper block 30 being angled.

By changing the radius of the circular portion of each yoke 11, 12, 31, 32, the vertical displacement, horizontal displacement, and angular displacement of the cage 100 may be adjusted. For example, in FIGS. 3A-3C, the circular portion of the distal yokes 11 on the lower block 10 is the larger than the radius of the circular portion of the distal yokes 31 of the upper block 30, and both are larger than the proximal yokes 12, 32. The larger radiuses will result in a larger potential increase in height, which will be the sum of the radiuses, than the potential height increase of the proximal yokes 12, 32, which have a smaller sum of radiuses. Therefore, adjusting radius sizes of the circular portions of each yoke 11, 12, 31, 32 can individually affect the vertical displacement of the proximal and distal ends of the upper block 30 relative to the lower block 10. This can also be considered from a linkage 51, 52 point of view. The length of the distal linkage 51, from pivot point 13 to pivot point 33, is the sum of the radius of both the circular portions of both distal yokes 11, 31. Accordingly, the range of motion is based on the length of the linkages 51, 52 which rotate around the connected hinge pins 13, 14, 33, 34.

FIGS. 3A-3C shows a progression of the cage's 100 range of motion. FIG. 3A shows the cage 100 in a fully compressed configuration. The cage 100 will be set to this configuration for insertion and removal from the spine. As seen in FIG. 3A, the yokes 11, 12, 31, 32 are seated within each other and the hinge pins 13, 14, 33, 34 are aligned, thus resulting in no angular displacement and a height of 8 mm.

When the screw 41 is rotated, the nut 42 pushes the cam follower surfaces 35 of the upper block 30 along the cam surfaces 15 of the lower block 10. As previously discussed, the movement of the upper block 30 relative to the lower block 10 is based on the length between the pivot points of the linkages 51, 52. Accordingly, the initial movement of the upper block 30 relative to the lower block 10 is primarily vertical displacement, since the linkages 51, 52 are moving from 3 o'clock to 2 o'clock and 3 o'clock to 1.5 o'clock positions, respectively. Since the linkage 51 is longer than the linkage 52, the distal end of the upper block 30 will gain more height than the proximal end, resulting in angular displacement. At the position shown in FIG. 3B, the distal end of the upper block 30 has been displaced vertically 2.9 mm, resulting in a cage height at that point of 10.9 mm, the horizontal displacement of the upper block 30 is 1.4 mm, and the angular displacement 3.7 degrees, relative to the lower block.

In the latter half of the extension cycle; the linkage 52 moves from approximately a 1.5 o'clock to 12 o'clock position, which results in more horizontal displacement and less vertical displacement, and the linkage 51 moves from approximately a 2 o'clock to 1 o'clock position, which is approximately equal parts vertical and horizontal displacement. Therefore, the angular displacement of the upper block 30 relative to the lower block 10 continues to increase. Accordingly, at full expansion, the distal end of the upper block 30 has increased in height 4.7 mm, resulting in a cage height at the point of 12.7 mm, the distal end of the upper block 30 has moved horizontally 3.9 mm, and the angular displacement of the upper block 30 is 8.1 degrees, relative to the lower block 10. The range of motion shown in FIGS. 3A-3C is only presented for exemplary purposes. As previously discussed, the yoke 11, 12, 31, 32 sizes, and associated linkage 51, 52 sizes, can be adjusted for different expansion characteristics.

The cage 100 allows for distraction, reduction, and lordosis of vertebra. Distraction is provided by the vertical displacement of the upper block 30 relative to the lower block 10, reduction is provided by horizontal displacement of the upper block 30 relative to the lower block 10, and lordosis is provided by the angular displacement of the upper block 30 relative to the lower block 10. As discussed above, the initial expansion of the cage 100 from a fully compressed position primarily distracts, due to the primarily vertical movement of the upper block 30, which then transitions into reduction and lordosis through the range of motion. The magnitude of distraction, reduction, and lordosis can be changed by using different length linkages 51, 52, and accordingly, differently sized yokes 11, 12, 31, 32 that match the linkage 51, 52 lengths. That is, changing the size of the yokes 11, 12, 31, 32 on the cam and cam follower surfaces 15, 35 will result in different amounts of distraction, reduction, and lordosis throughout the range of motion of the cage 100. Therefore, cage 100 can be customized for users that require specific amounts of distraction, reduction, and lordosis.

Figure 4A:
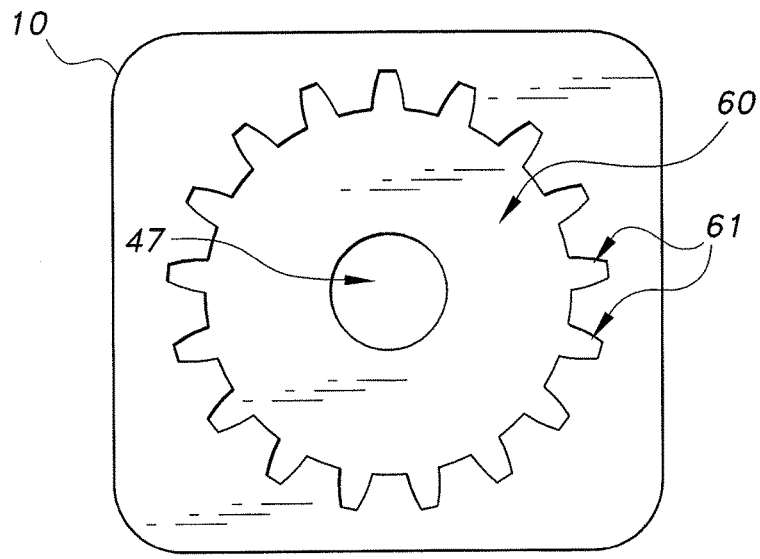
FIG. 4A is a front view of the lower block, shown without the screw attached.
Figure 4B:
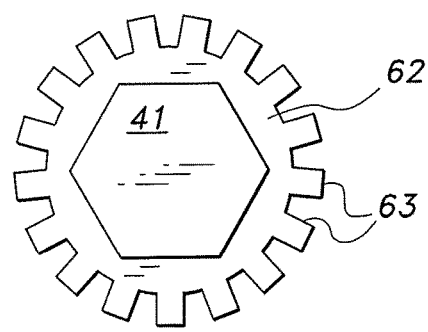
FIG. 4B is a top view of a screw with attached screw head gear for use with the block of FIG. 4A.
Figure 4C:
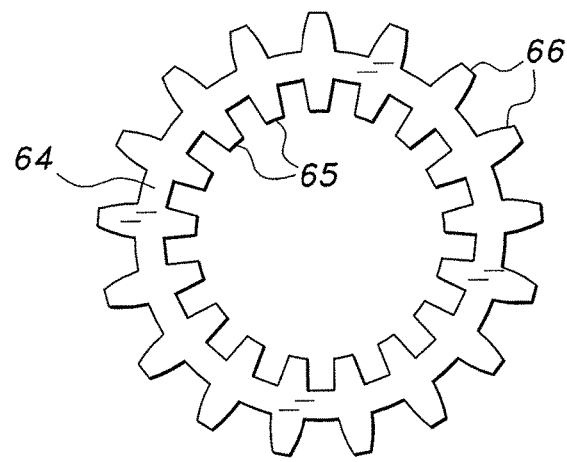
FIG. 4C is a front view of a locking gear for use with the block of FIG. 4A.
Figure 4D:
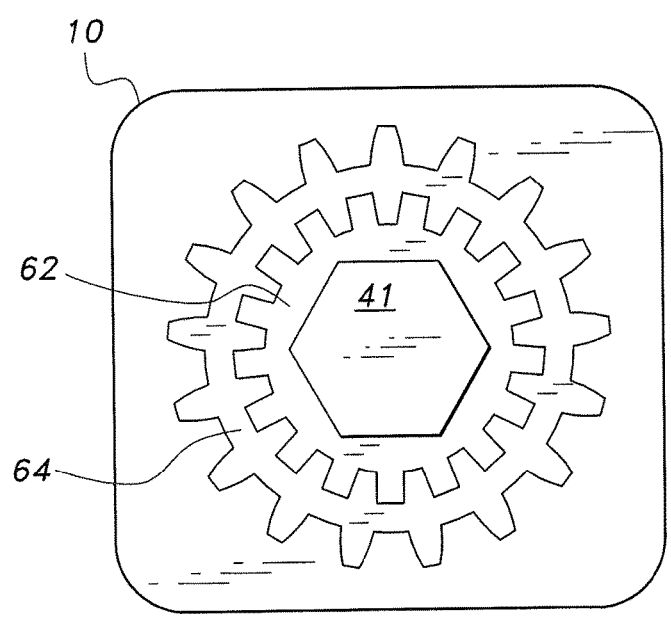
FIG. 4D is a front or proximal view of the lower block of FIG. 4A, shown including the screw and locking mechanism of FIGS. 4B-C.

Once the practitioner has expanded the cage 100 to a desired point, the upper block 30 and lower block 10 can be locked at that position. FIGS. 4A-4D show a mechanism for locking the cage at a set expansion level by locking axial rotation of the screw 41. FIG. 4A shows the screw hole 47 and locking mechanism 60 of the lower block 10 without the screw 42 inserted. The portion of the locking mechanism 60 defined by the lower block 10 includes an indentation surrounding the screw hole 47 having a radial dispersion of cage gear roots 61. FIG. 4B shows the screw 41 head and attached screw head gear 62. The screw head gear 62 is attached to the screw 41 immediately below the head and is axially locked with the screw 41. The screw head gear 62 includes gear roots 63 radially dispersed along its circumference. FIG. 4C shows a locking gear 64 that is used to lock the screw head gear 62 to the cage gear roots 61 of the lower block 10. Accordingly, the gear roots 65 in the inner circumference of the locking gear 64 match with the gear head roots 63 on the screw head gear 62, and the gear roots 66 on the outside circumference match with the cage gear roots 61 in the lower block 10. As seen in FIG. 4D, locking gear 64 is meshed with the cage gear roots 61 of the lower block 10, thus axially locking it relative to the lower block 10. The gear roots 63 of the screw head gear are meshed with the inner gear roots 65 of the locking gear 64, thus axially locking the screw 41 to the locking gear 64 and the lower block 41. The locking gear 64 may be held in place by a friction fit. To lock the locking gear 64 in place, the practitioner can force it into the gear roots of the lower block and screw head 61, 63, which are sized for a tight friction fit. The locking gear may include hooks, a flange, a tab, or holes for connecting a tool to pull out the locking gear for screw adjustment.

It is to be understood that expandable intervertebral cage is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An expandable intervertebral cage comprising:
a lower block having left and right proximal yokes and left and right distal yokes, the lower block having a lower channel portion defined therein extending between the left and right yokes, each of the lower block yokes defining left and right cam surfaces;
an upper block having left and right proximal yokes and left and right distal yokes, the upper block having an upper channel portion defined therein extending between the left and right yokes, each of the upper block yokes defining left and right cam follower surfaces, the upper and lower block each having a bone contacting surface adapted for engaging vertebrae on a patient's spine;
a left proximal linkage connecting the left proximal yokes, a right proximal linkage connecting the right proximal yokes, a left distal linkage connecting the left distal yokes, and a right distal linkage connecting the right distal yokes; each of the linkages maintaining contact between the cam and cam follower surfaces for at least 90 degrees of rotation;

a screw extending through the lower block and into the lower channel portion between the lower block left and right yokes; and a nut wedged between the upper block and the lower block, the screw engaging the nut so that rotating the screw in a first direction causes the nut to separate the upper and lower block, and rotating the screw in an opposite direction causes the nut to compress the upper and lower blocks.

2. The expandable intervertebral cage of claim 1, further comprising left and right flanges defined on opposing sides of the upper channel portion of the upper block, the flanges being angled relative to the bone contacting surface of the upper block and being disposed parallel to each other, the flanges being configured to bear against the nut.

3. The expandable intervertebral cage of claim 2, wherein the upper block has left and right grooves defined on opposing sides of the upper channel portion, the grooves extending parallel to the flanges.

4. The expandable intervertebral cage of claim 3, wherein the nut has left and right posts extending outward into the left and right grooves.

5. The expandable intervertebral cage of claim 1, wherein each of the left and right distal linkages are longer than each of the left and right proximal linkages.

6. The expandable intervertebral cage of claim 1, wherein each of the lower block and upper block yokes defines a surface having a partially circular shape having a center, each of said linkages being rotatably connected to the lower block and upper block yokes at the center of the circles.

7. The expandable intervertebral cage of claim 1, further comprising two screw locking posts extending through the lower block transverse to the screw, the screw having an annular groove defined therein, the screw locking posts being seated in the annular groove to temporarily prevent further axial movement of the screw.

8. The expandable intervertebral cage of claim 1, wherein the upper block has proximally pointed spikes on the bone contacting surface of the upper block and the lower block has distally pointed spikes on the bone contacting surface of the lower block.

9. The expandable intervertebral cage of claim 1, wherein the lower block has a groove formed in the lower channel portion, the nut being configured to slide along the groove when the screw is turned.

10. An expandable intervertebral cage comprising:
a lower block defining a cam surface;
an upper block defining a cam follower surface;
a plurality of linkages configured to maintain contact between the cam surface and cam follower surface through at least 70 degrees of linkage rotation;
a screw extending through the lower block; and
a nut wedged between the upper block and the lower block, the screw engaging the nut so that rotating the screw in a first direction causes the nut to separate the upper and lower block, and rotating the screw in an opposite direction causes the nut to compress the upper and lower blocks.

11. The expandable intervertebral cage of claim 10, wherein the cam surface includes two projections defining a portion of a circle having a center and the cam follower surface includes two projections defining a portion of a circle having a center.

12. The expandable intervertebral cage of claim 10, wherein the upper block has opposing grooves defined therein, the nut including two posts slidably disposed in the grooves defined in the upper block.

13. The expandable intervertebral cage of claim 10, wherein the plurality of linkages includes proximal and distal linkages, the proximal and distal linkages having different lengths.

* * * * *